(12) United States Patent
Chartrain et al.

(10) Patent No.: US 6,171,832 B1
(45) Date of Patent: Jan. 9, 2001

(54) PROCESS FOR THE PREPARATION CIS-(1S, 2R)-INDANEDIOL BY DIREDUCTION OF 1,2-INDANEDIONE USING TRICHOSPORON CUTANEUM

(75) Inventors: Michael M. Chartrain, Westfield; Norihiro Ikemoto, Edison; Anthony O. King, Somerville, all of NJ (US)

(73) Assignee: Merck & Co., Inc., Rahway, NJ (US)

( * ) Notice: Under 35 U.S.C. 154(b), the term of this patent shall be extended for 0 days.

(21) Appl. No.: 09/300,344

(22) Filed: Apr. 27, 1999

Related U.S. Application Data

(60) Provisional application No. 60/083,355, filed on Apr. 28, 1998.

(51) Int. Cl.$^7$ ................................ C12P 7/22; C07C 1/04
(52) U.S. Cl. ........................ 435/156; 435/280; 435/911
(58) Field of Search ................................ 435/280, 156, 435/911

(56) References Cited

U.S. PATENT DOCUMENTS

| | | | |
|---|---|---|---|
| 5,413,999 | 5/1995 | Vacca et al. | 514/231.5 |
| 5,605,819 | 2/1997 | Chartrain et al. | 435/123 |
| 5,858,737 | 1/1999 | Buckland et al. | 435/129 |

FOREIGN PATENT DOCUMENTS

| | | |
|---|---|---|
| WO 97/00966 | 1/1997 | (WO) . |
| WO 98/06865 | 2/1998 | (WO) . |
| WO 98/06866 | 2/1998 | (WO) . |

OTHER PUBLICATIONS

E. N. Jacobsen et al., "Highly Enantioselective Epoxidation Catalysts Derived from 1,2–Diaminocyclohexane", J. Amer. Chem. Soc., vol. 113, pp. 7063–7064 (1991).

K. Tomioka et al., "Stereoselective Reactions. XIX. Asymmetric Dihydroxylation of Olefins . . . ", Chem. Phar. Bull., vol. 38, pp. 2133–2135 (1990).

L. P. Wackett et al., "Benzylic Monooxygenation Catalyzed by Toluene Dioxygenase from Pseudomonas putida", Biochemistry, vol . 27, pp. 1360–1367 (1988).

J. M. Brand et al., "Stereospecific Hydroxylation of Indan by Escherichia coli Containing the Cloned . . . ", Appl. Environ. Microbiol., vol. 58, No. 10, pp. 3407–3409 (Oct. 1992).

J. B. Jones, "Enzymes in Organic Synthesis", Tetrahedron, vol. 42, No. 15, pp. 3351–3403 (1986).

M. D. Lilly, "Advances in Biotransformation Processes", Chem. Eng. Sci., vol. 49, No. 2, pp. 151–159 (1994).

O. P. Ward et al., "Reductive biotransformations of organic compounds by cells or enzymes of yeast", Enzyme Microb. Technol., vol. 12, pp. 482–493 (1990).

S. M. Roberts et al., "The Use of Enzymes for the Preparation of Biologically Active Natural Products and Analogues in Optically Active Form", Current Organic Chem., vol. 1, pp. 1–20 (1997).

M. Chartrain et al., "The Application of Asymmetric Bioreductions of the Production of Chiral Pharmaceutical Drugs", Enzyme Engineering XIII, Annals of NY Acad. Sciences, vol. 799, pp. 612–619 (1996).

R. Bel–Rhlid et al., "Microbiological Reduction of Carbonyl Groupings: Preparation of Stereoisomeric Acyclic Chiral Alpha Diols", Biocatalysis, vol. 6, pp. 319–337 (1992).

W. Hummel, "New Alcohol Dehydrogenases for the Synthesis of Chiral Compounds", Adv. Biochem. Eng./Biotechnology, vol. 58, pp. 147–179 (1997).

R. Pereira, "Baker's Yeast: Some biochemical aspects and their influence in biotransformations", Appl. Biochem. and Biotechnology, vol. 55, pp. 123–132 (1995).

R. Csuk, "Baker's Yeast Mediated Transformations in Organic Chemistry", Chem. Rev., vol. 91, pp. 49–97 (1991).

K. Nakamura et al., "Asymmetric Reduction of Ketones with Microbes", Bull. Inst. Chem. Res., vol. 67, pp. 157–168 (1989).

T. Kometani et al., "Large–scale production of chiral alcohols with baker's yeast", J. Mol. Cat. B: Enzymatic., vol. 1, pp. 45–52 (1996).

M. Chartrain et al., "Asymmetric bioreduction of cyclohexylphenyl ketone to its corresponding alcohol . . . ", J. of Ferm. and Bioeng., vol. 83, pp. 395–396 (1997).

J. Reddy et al., "Asymmetric bioreduction of a beta–tetralone to its corresponding (S)–alcohol by the Yeast Trichosporon capitautum MY 1890", J. of Ferm. and Bioeng., vol. 81, pp. 304–309 (1996).

J. R. Hunt et al., "Yeast catalyzed reduction of beta–keto esters. I. Factors affecting whole–cell catalytic activity and stereoselectivity", Biocatalysis and Biotransformation, vol. 12, pp. 159–178 (1995).

*Primary Examiner*—Sandra E. Saucier
(74) *Attorney, Agent, or Firm*—Kenneth R. Walton; Melvin Winokur

(57) ABSTRACT

A process for preparing cis-(1S,2R)-indanediol is disclosed. The process comprises (A) fermenting a culture medium containing a yeast strain selected from the group consisting of Trichosporon cutaneum MY 1506 (ATCC 74440) and mutants thereof and 1,2-indanedione to form cis-(1S,2R)-indanediol; and (B) recovering cis-(1S,2R)-indanediol from the culture medium. A process for preparing (1S)-amino-(2R)-indanol from the recovered cis-(1S,2R)-indanediol via the Ritter reaction is also disclosed.

10 Claims, 3 Drawing Sheets

PROCESS FOR THE PREPARATION CIS-(1S, 2R)-INDANEDIOL BY DIREDUCTION OF 1,2-INDANEDIONE USING TRICHOSPORON CUTANEUM

This application claims the benefit of Ser. No. 60/083,355 filed Apr. 28, 1998.

FIELD OF THE INVENTION

The invention relates to the bioconversion of 1,2-indanedione to cis-(1S,2R)-indanediol which is useful as a precursor to (1S)-amino-(2R)-indanol, which in turn can be employed an intermediate in the synthesis of Crixivian® (also referred to an indinavir), a potent HIV protease inhibitor.

BACKGROUND OF THE INVENTION

The present invention is concerned with a process for synthesizing intermediates for compounds which inhibit the protease encoded by human immunodeficiency virus (HIV), and in particular certain oligopeptide analogs, such as Compound J (i.e., indinavir) and other compounds as described in U.S. Pat. No. 5,413,999. These compounds are of value in the prevention of infection by HIV, the treatment of infection by HIV and the treatment of the resulting acquired immune deficiency syndrome (AIDS). These compounds are also useful for inhibiting renin and other proteases.

1(S)-Amino-2(R)-hydroxy indan of the structure

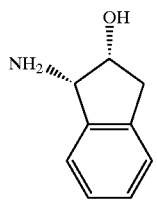

is used to form an amide sidechain group on Compound J, a potent inhibitor of HIV protease, via methods described in U.S. Pat. No. 5,413,999 and in Merck 19464IA, U.S. Ser. No. 08/696,667, filed Aug. 14, 1996, both of which are incorporated herein by reference in their entireties.

Previous attempts at synthesis involve inefficient production of the racemate 1(+/−)amino-2(+/−) hydroxy indan from the racemic indene oxide. Other attempts at synthesis involve bioconversion of indene with a fungal haloperoxidase to give predominantly trans-(2S,1S)-bromoindanol, which is then subjected to various chemical steps to give (1S)-amino-(2R)-indanol. Still other attempts at synthesis relate to chemical synthesis with racemic epoxidation of indene as an intermediate step, followed by resolution with L-tartaric acid. Indene epoxide with a high enantiomeric excess can be obtained from indene via Jacobson's S,S-salen manganese catalyst (Jacobsen et al., *J. Am. Chem. Soc.,* vol. 113, 7063–7064 (1991)), but upon hydroxylation to open the epoxide ring only a trans-diol is produced.

The chemical synthesis of cis-indanediols via the asymmetric oxidation of indene has been reported, but only in low enantiomeric excess. Tomoka et al., *Chem. Pharm. Bull.,* vol. 38, 2133–2135 (1990), for example, discloses the formation of 1S,2R-indanediol in 30% enantiomeric excess via oxidation of indene using a stoichiometric amount of an osmium tetroxide-chiral amine complex at −78° C. Resolution of the indanediol product would be required in order to prepare an enantiomeric derivative such as ((S)-amino-(2R)-indanol.

U.S. Ser. No. 08/696,667 discloses an improved synthetic method in which the tartaric acid resolution step is eliminated. The method of U.S. Ser. No. 08/696,667 involves the stereoselective bioconversion of indene to cis-(1S,2R)-indanediol by the action of the enzyme dioxygenase, followed by further chemical treatment of the indanediol (e.g., treatment with a nitrite in the presence of acid in accordance with the Ritter reaction) to give (1S)-amino-(2R)-indanol. Preferred sources for the enzyme dioxygenase disclosed in U.S. Ser. No. 08/696,667 include *Pseudomonas putida* 421-5 (ATCC 55687) and Rhodococcus B264-1 (ATCC 55806).

While the route disclosed in USSN 08/696,667 constitutes a practical means for the production of a cis-(1S,2R)-indanediol intermediate, other indene metabolites such as indanone, indenol and keto-hydroxy compounds can form as by-products, which can both limit the yield and complicate the recovery of the desired indanediol product. The maximum isolated yield of cis-(1S,2R)-indanediol in the 08/696,667 process is typically no more than about 20%, which in turn limits the potential yield of the (1S)-amino-(2R)-indanol derivative. There exists the need for bioconversion processes which produce cis-(1S,2R)-indanediol from indene in higher yields and with little or no by-product formation.

SUMMARY OF THE INVENTION

The present invention is a method for preparing cis-(1S-2R)-indanediol via the microbial direduction of 1,2-indanedione. More particularly, the present invention is a process for preparing cis-(1S-2R)-indanediol comprising (A) fermenting a culture medium containing a yeast strain selected from the group consisting of *Trichosporon cutaneum* MY 1506 (ATCC 74440) and mutants thereof and 1,2-indanedione to form cis-(1S,2R)-indanediol; and (B) recovering cis-(1S,2R)-indanediol from the culture medium.

The method of the present invention does not form indanedione, indenol or keto-hydroxy compounds as by-products and can have isolated yields of cis-(1S,2R)-indanediol of 50% or more.

In one embodiment, the step of recovering the cis-(1S, 2R)-indanediol comprises separating the cis-(1S,2R)-indanediol from trans-indanediol diastereomer byproducts (i.e., trans-(1S,2S)-indanediol and/or trans-(1R,2R)-indanediol.) In another embodiment of the invention, the recovery step further comprises separating the cis-(1S,2R)-indanediol from its cis-(1R,2S)-indanediol enantiomer, such that the separated cis-(1S,2R) enantiomer formed is essentially free of any stereoisomer.

In a preferred embodiment of the invention, the cis-(1S, 2R)-indanediol is formed with an enantiomeric excess of at least about 99%. Enantiomeric excess is the percent excess of one enantiomeric form over the other. Accordingly, the enantiomeric excess of enantiomeric form A over enantiomeric form B is [(A−B)/(A+B)]×100.

In another preferred embodiment of the invention, the yeast strain is *Trichosporon cutaneum* MY 1506 (ATCC 74440).

A further aspect of the present invention is a process for preparing (1S)-amino-(2R)-indanol comprising (A) fermenting a culture medium containing a yeast strain selected from the group consisting of *Trichosporon cutaneum* MY 1506 (ATCC 74440) and mutants thereof and 1,2-indanedione to form cis-(1S,2R)-indanediol; (B) recovering cis-(1S,2R)-indanediol from the culture medium; (C) mixing one equivalent of the recovered cis-(1S,2R)-indanediol with excess acetonitrile and maintaining the mixture at a temperature of from about −40° C. to about 25° C.; and (D) adding to the mixture excess equivalents of strong acid and maintaining the mixture at a temperature of from about −40° C. to about 25° C. to form (1S)-amino-(2R)-indanol.

Figure 1:
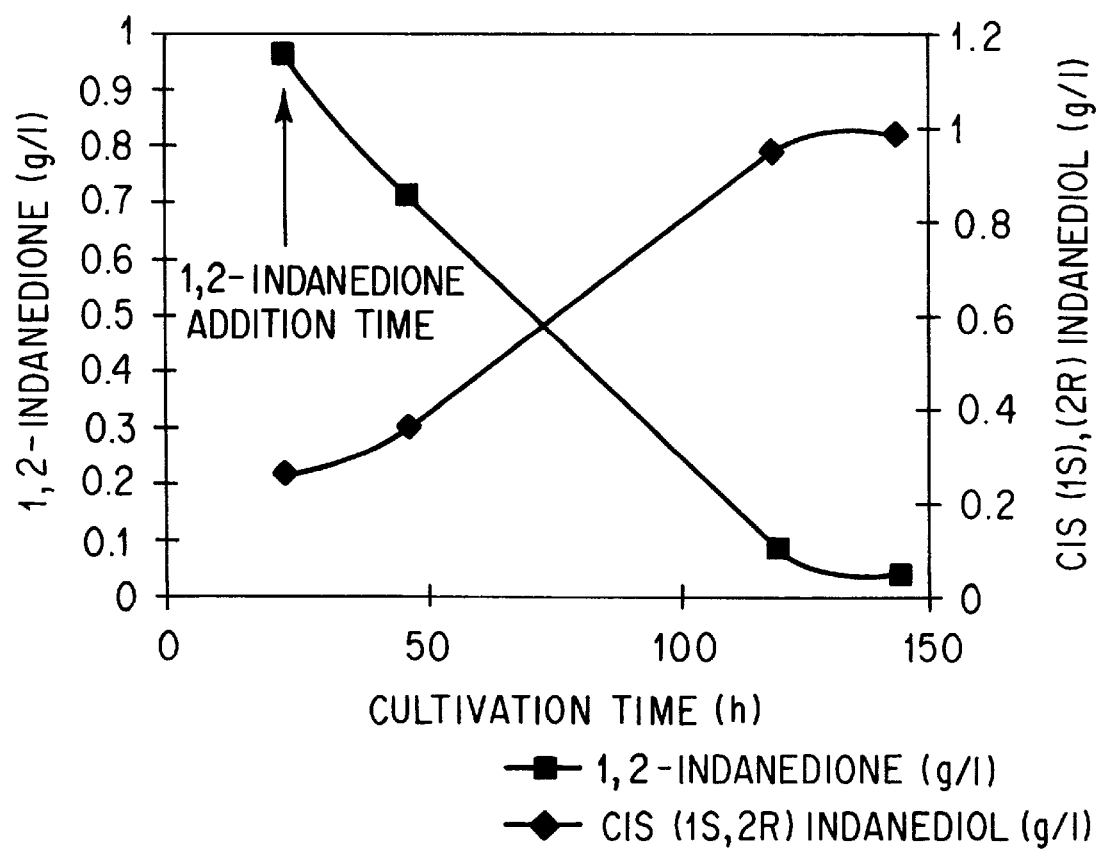
FIG. 1 is a plot of the 1,2-indanedione concentration and cis-(1S,2R)-indanediol concentration versus cultivation time for the shaker flask scale bioconversion set forth in Example 2.

DETAILED DESCRIPTION OF THE INVENTION 1,2-indanedione can be prepared according to the following scheme:

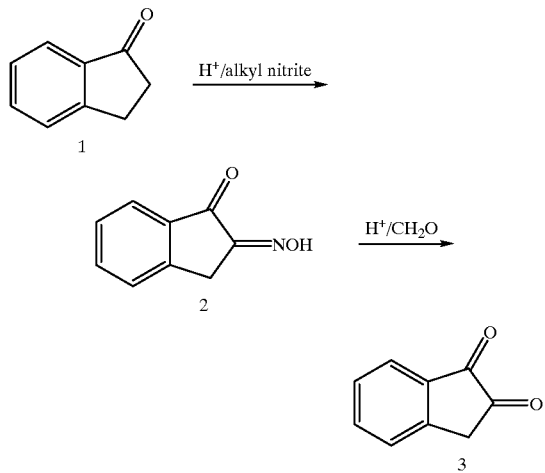

In the scheme (adapted from Cava et al., *J. Am. Chem. Soc.*, vol.80, 2255–2257 (1958)), 1-indanone(1) is treated with a lower alkyl nitrite (e.g., butyl nitrite) under acidic conditions to obtain 2-oximino-1-indanone (2), which is subsequently reacted with formaldehyde under highly acidic conditions to form 1,2-indanedione (3). 1,2-indanedione is converted to cis-(1S,2R)-indanediol by addition of the indanedione to a culture medium containing the yeast strain *Trichosporon cutaneum* MY1506, or a mutant thereof, and fermenting the mixture for a time and under conditions effective to form the desired indanediol.

A sample of the *Trichosporon cutaneum* MY 1506 was deposited under the Budapest Treaty at the American Type Culture Collection (ATCC), 12301 Parklawn Drive, Rockville, Md. 20852 on Apr. 15, 1998. The culture access designation is ATCC 74440. This deposit will be maintained in the ATCC for at least 30 years and will be made available to the public upon the grant of a patent disclosing it. The availability of a deposit does not constitute a license to practice the subject invention in derogation of patent rights granted by government action.

The physical characteristics and taxonomy, including morphological, cultural, biological and physiological characteristics of MY 1506 (ATCC 74440) are briefly described as follows: Growth occurs at both 27° C. and 37° C. on yeast malt extract agar, Sabouraud's dextrose agar, Sabouraud's maltose agar, and trypticase soy agar. Culture is mature in 48 hours. Colonies are white to cream-colored with a rough surface, entire margin, butyrous texture, and mild fragrance. Hyphae are septate and 20–30 $\mu m \times 2$–3 $\mu m$. Vegetative reproduction by budding and splitting was observed. Cylindrical arthroconidia 2–3 $\mu m \times 8$–10 $\mu m$ were also observed.

Mutants of MY 1506 suitable for use in the process of the invention can be prepared via techniques known in the art, including chemically induced mutagenesis using mutagens such as 1-methyl-3 nitro-1-nitrosoguanidine, ethyl methane sulfonate, 2-aminopurine, or the like, and radiation induced mutagenesis generated by a UV light source such as a germicidal lamp or γ-irradiation from a cobalt-60 source.

The culture medium is defined as a mixture which supports the growth of the yeast strain MY 1506 (ATCC 74440) or a mutant thereof. The culture medium for carrying out the fermentation typically has a carbon source and a nitrogen source. Preferred sources of carbon in the culture medium are carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients; are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

A preferred culture medium is Sabouraud dextrose broth (available commercially from Difco of Detroit, Mich., USA) which is an aqueous solution of glucose (10 grams/liter) and neopeptone (20 grams/liter).

Submerged aerobic cultivation conditions are preferred for the production of cells in massive amounts. A shaking culture in a flask is employed for cell production in small amounts. When the growth is carried out in large tanks, it is desirable first to produce an inoculum of the organism by inoculating a relatively small quantity of culture medium with the organism stored at about −20 to about 70° C. and culturing said inoculated medium, also called the "seed medium", and then to transfer the resulting inoculum aseptically to large tanks. The fermentation medium, in which the inoculum is produced, is generally autoclaved to sterilize the medium prior to inoculation. The pH of the medium is typically adjusted to about 7.0 prior to the autoclaving step.

Agitation and aeration of the culture mixture may be accomplished in a variety of ways. Agitation may be provided by impeller or similar mechanical agitation equipment, shake flask bioreactor, by various pumping equipment or by the passage of sterile air through the medium. Aeration may be effected by passing sterile air through the incubation mixture.

The fermentation is usually conducted at a temperature of from about 25° C. to about 37° C., preferably about 30° C., for a period of from about 0.5 to about 5 days, preferably about 2 days, which may be varied according to cultivation conditions and scales. Preferably, the production cultures are incubated for about 2 days at about 30° C. in a stirred bioreactor operating at an impeller speed of about 300 rpm.

The product cis-(1S,2R)-indanediol is in the aqueous phase of the culture media, and accordingly can be recovered (i.e., isolated and purified) by conventional methods such as centrifugal or gravitational clarification of the aqueous phase, concentration under reduced pressure, extraction with a conventional solvent, such as isopropyl acetate and the like, pH adjustment, treatment with a conventional resin (e.g., anion or cation exchange resin, non-ionic resin, etc.), treatment with a conventional adsorbent (e.g., activated charcoal, silica gel, cellolose, alumina, etc.), crystallization, recrystallization, and the like.

A preferred sequence of recovery methods includes solvent extraction of the aqueous phase with a suitable organic solvent (e.g., ethyl or isopropyl acetate); separation, drying, and filtration of the organic layer; evaporative removal of the organic solvent; and chromatographic purification.

The recovered cis-(1S,2R)-indanediol product typically has an enantiomeric excess of at least about 99%. While further resolution is often not required, the recovered cis-(1S,2R)-indanediol can be subjected to chiral specific crystallization to increase the chiral purity by rejection of the undesired 1R,2S stereoisomer in the mother liquors. For example, a dried, filtered acetate extract obtained by solvent extraction of the aqueous phase can be vacuum concentrated to ~30 g cis-indanediol/liter and then filtered through a medium porosity glass filter to remove any particulate. The filtered extract can then be further concentrated to a final concentration of about 200 g cis-indanediol/liter. The cis-indanediol begins to crystallize during the final concentration step and the crystallization is completed by cooling to about 5–10° C. and aging a minimum of about 8 hours. The crystals can either be filtered, washed with isopropyl acetate/hexane (1:1), then hexane, and dried under vacuum. cis-Indanediol with greater than about 99.5% enantiomer excess of the 1S,2R form can thereby be obtained.

cis-(1S)-Amino-(2R)-indanol can be prepared from cis-(1S,2R)-indanediol via the Ritter reaction. Reaction of the cis-(1S,2R)-indanediol with acetonitrile, followed by hydrolysis in the presence of water, is carried out rapidly. About one equivalent of solid cis-(1S,2R)-indanediol is dissolved in excess acetonitrile, with or without organic solvent. A typical solvent is dichloromethane.

The mixture of cis-(1S,2R)-indanediol and acetonitrile is then contacted with excess equivalents of strong acid, such as triflic acid, methanesulfonic acid or sulfuric acid. Typically about two equivalents of strong add are added. Since the addition of add to the diol-acetonitrile mixture is exothermic, cooling is typically carried out before contacting with strong acid. After from about one to about two hours, excess water equivalents are added. The remaining acetonitrile is removed by distillation or refluxing, to give a Ritter solution.

The resulting cis-(1S)-amino-(2R)-indanol is substantially free of the stereoisomer trans-aminoindanol. Typically, resolution is not needed in subsequent steps.

The Ritter solution then may be subjected to various purification treatments to remove acid contaminants, such as the following:

(a) Reverse Ion Pair Extraction: Base is added to neutralize the acid, and then raise the pH to about 12 or higher, to give a basified Ritter solution. This basified Ritter solution is extracted with any organic solvent having a suitable solubility for cis-aminoindanol; e.g. methylene chloride, ethyl acetate or 1-butanol, preferably 1-butanol. The aqueous layer(s) then may be discarded.

To the organic layer(s) containing cis-aminoindanol is added a suitable acid in excess of cis-aminoindanol equivalents. Suitable acids will form a salt complex with cis-aminoindanol and make the cis-aminoindanol more soluble in aqueous solution. Such suitable acids include but are not limited to L-tartaric, D-tartaric, meso-tartaric, ascorbic, malonic, citric, formic acids, HCl, preferably L-tartaric acid.

The resulting salt in organic solvent is then extracted with an aqueous solution, e.g., water, to give an aqueous extract. Titration of base equivalents into the aqueous extract will give crystallization beginning at about pH 8–9. Crystallization is typically complete before titration with base reaches pH of about 11–12. The resulting (1S)-amino-(2R)-indanol is substantially pure.

(b) Cation Exchange Chromatography: Alternatively, the Ritter solution may be subjected to cation exchange chromatography to remove acid contaminants. Any cation exchange resin is suitable, but; typically comprises styrene-divinylbenzene resin, with acid groups such as sulfonic acid or carboxylic acid attached thereto.

The resin is mixed with the Ritter solution, then washed with water or other aqueous solvent to remove unwanted acid. The bound cis-aminoindanol is eluted by the steps of adding base (to increase pH to keep cis-aminoindanol soluble), followed by elution with any one of a variety of solvents, e.g. methanol, acetonitrile or THF in water. The basification-elution cycle may be repeated several times to quantitatively elute cis-aminoindanol off the resin. The resulting (1S)-amino-(2R)-indanol is substantially pure.

EXAMPLES

The following examples serve only to illustrate the process of the invention and procedures related thereto. These examples are not to be construed as limitations on the scope of the invention.

All chemicals used in the following examples were of reagent grade and were purchased commercially.

Example 1

Preparation of 1,2-Indanedione

1-Indanone (100 g, 0.757 mol) was dissolved in 2-methoxyethanol (600 mL) in a 2 L round bottom flask equipped with a overhead mechanical stirrer. The mixture was cooled over an ice bath, and concentrated aqueous HCl (200 mL) was added. Butyl nitrite (50 mL, 0.428 mol) was added, and after 1 minute when precipitate began to form, more butyl nitrite (50 mL, 0.428 mol) was added. The mixture was stirred for 15 min. more and then poured into ice water (8 L). The solid was filtered on a sintered funnel and rinsed with 8 L water. The solid was dissolved in 2.5 L hot methanol, seeded with pure oxime, then allowed to cool to room temperature then over an ice bath. The yellow crystals were collected on a sintered funnel, rinsed with cold methanol, then dried overnight under vacuum to yield 2-oximino-1-indanone (92.8 g, 76% yield). The finely ground oxime (80 g, 0.496 mol) was suspended in 35% formaldehyde solution (160 mL) and concentrated HCl (320 mL) in a 2 L round bottom flask equipped with an overhead mechanical stirrer. The temperature was maintained initially at 15° C. with an ice bath, then the bath was removed and the reaction mixture was stirred vigorously for 30 min. The mixture was poured onto 2 L ice, the solid filtered and then rinsed with water. The yellow powder was dried in a vacuum oven to yield 55.0 g product, which was recrystallized from ether (5 L, 3 crops) to afford after oven drying pure diketone (37.3 g, 51% yield). The aqueous mother liquor yielded crystals of the oxime (9.5 g, 12% recovered starting material).

Example 2

Shake Flask Scale Preparation of cis-(1S,2R)-indanediol

A frozen suspension of *Trichosporon cutaneum* MY 1506 cells stored at −70° C. in 20% glycerol was thawed at room temperature. A 1.5 mL volume of the suspension was used to inoculate a 250-mL Erlenmeyer flask containing 50 mL of Sabouraud dextrose broth (30 g/L). The culture was aerobically incubated on an orbital shaker (200 rpm) for 48 h at 25° C. A 250-mL Erlenmeyer flask containing 50 mL of Sabouraud dextrose broth was inoculated with 1.5 mL of the 48 h seed and was aerobically incubated on an orbital shaker (200 rpm) for 24 h at 25° C. A 2-L Erlenmeyer flask containing 500 mL of Sabouraud dextrose broth was inoculated with 25 mL of the second-stage seed and was aerobically incubated on an orbital shaker (200 rpm) at 25° C. After 24 h of cultivation, bioconversion was initiated by adding 10 mL of an ethanol solution containing 0.5 g of 1,2-indanedione (final concentration 1.0 g/L) to the flask. The culture was returned to the same incubation conditions and bioconversion activity was monitored by regular sample collection. The 1,2-indanedione was bioconverted to cis- —(1S,2R)-indanediol over a 120 h incubation period, as shown in FIG. 1. Upon the addition of 1,2-indanedione during active cell growth, bioconversion initiated immediately and proceeded linearly for 120 h, with a cis-indanediol production rate of 6.66 mg/L/h. HPLC analysis indicated that a final cis-(1S,2R)-indanediol concentration of 0.991 g/L, representing a conversion yield of 99.1%, was achieved. Chiral analyses of the cis- —(1S,2R)-indanediol product indicated that under these bioconversion conditions, the enantiomeric excess of the cis- —(1S,2R)-indanediol was greater than 99%.

Example 3

23 Liter Scale Preparation of cis-(1S,2R)-Indanediol

Figure 2:
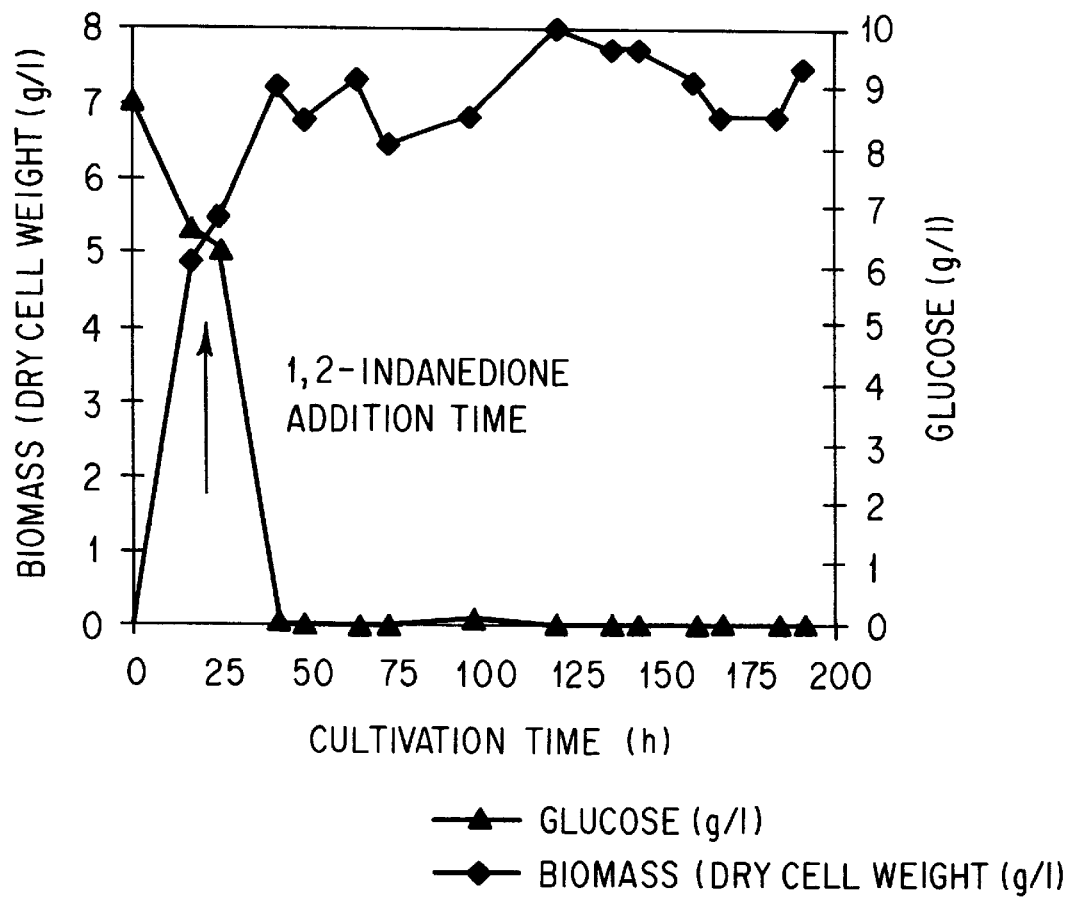
FIG. 2 is a plot of the biomass and glucose concentration versus cultivation time for the full scale bioconversion of 1,2-indanedione to cis-(1S,2R)-indanediol set forth in Example 3.
Figure 3:
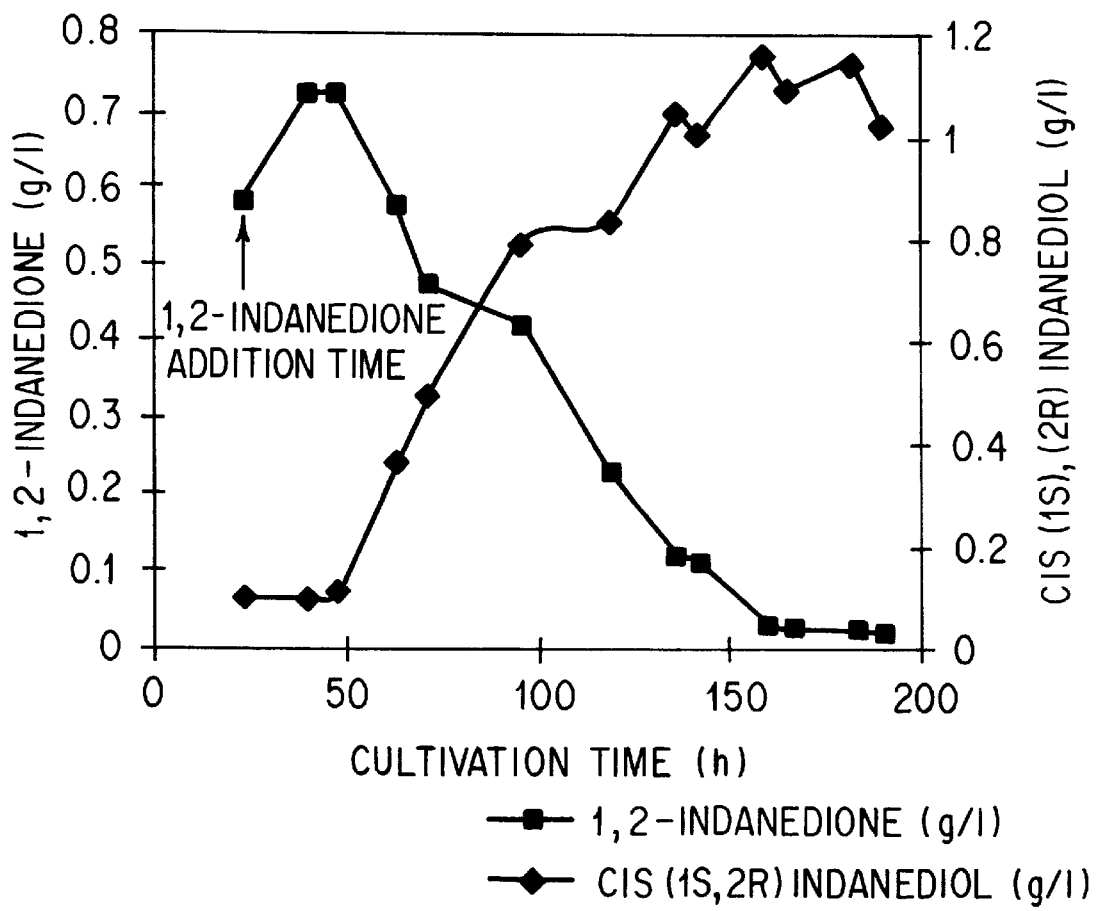
FIG. 3 is a plot of the 1,2-indanedione concentration and the cis-(1S,2R)-indanediol concentration versus cultivation time for the full scale bioconversion set forth in Example 3.

Scale-up of the bioconversion process was performed in a 23-L fermentor (Chemap Inc., South Plainfield, N.J., USA). A volume of 16-L of Sabouraud dextrose broth (30 g/L) and 16 mL of P2000 antifoam (Poly Glycol, Dow Chemical Co., Midland, Mich., USA) were sterilized in situ at 121° C. for 25 min. A volume of 750 mL of a 24-h old second stage seed (prepared as described in Example 2) was used to inoculate the bioreactor. The bioreactor was operated at 25° C. with an agitation set at a minimum of 400 rpm, an aeration of 6 L of air per minute, and a back pressure of 1.0 bar. Dissolved oxygen tension was maintained at 30% of initial saturation by computer controlled ramping of the agitation and by manually increasing the air flow. After 24 h of cultivation and once active growth was completed as indicated by both a quasi complete glucose consumption and by a drop in respiratory activity to about 1 mM/L/h, 16 g of 1,2-indanedione in 320 mL of ethanol was added to the fermentor (final concentration of 1.0 g/L). See FIG. 2. Upon addition of 1,2-indanedione to the fermentor, the bioconversion initiated immediately and proceeded steadily for about 100 h, with a cis-indanediol production rate of 6.80 mg/L/h. Over the next 90 hours, the bioconversion rate remained relatively stable, as shown in FIG. 3. The reactor was operated under the same conditions as described above for the duration of the bioconversion. During this time course there was a transient appearance of an intermediate, which was probably the keto-hydroxy intermediate compound, as indicated by an HPLC reverse phase retention time which was similar to that of an authentic standard. HPLC analysis showed that a peak cis- (1S,2R)-indanediol titer of 0.988 g/L was achieved during this scale up. Super critical fluid chromatography analyses of the purified cis-(1S,2R) and trans-(1S,2S) indanediol demonstrated that the enantiomeric excesses during this bioconversion scale up were 99% and 26%, respectively.

Example 4

Analytical Methods

Reverse phase assay - A Rainin HPLC system (Rainin, Woburn, Mass., USA) equipped with a Zorbax RX-C8 column (4.6 mm ×25 cm) (Mac-Mod Analytical, Chadds Ford, Pa., USA), was employed for the separation of 1,2-indanedione and indanediol. Separation was achieved by a 10–90% gradient employing a mobile phase of acetonitrile and acidified water (0.1% phosphoric acid) at a flow rate of 1 mL/min for 30 min. Detection was performed at 220 nm.

Chiral assay - A Rainin HPLC system (Rainin, Woburn, Mass., USA) was used for this assay. A normal phase Chiralpak AD column (250×4.6 mm) (Chiral Technologies) was employed for the separation of the two cis- indanediol enantiomers using a solvent system comprised of 90% hexane and 10% ethanol. The solvent was delivered isocratically at a flow rate of 0.9 mL/min and detection was performed at 220 nm. Under these conditions, the cis-(1R, 2S) indanediol and the cis-(1S,2R)-indanediol eluted after 12.9 and 14.5 min. respectively.

A Super Critical Fluid Chromatography $CO_2$ system (Gilson, Middleton, Wis., USA) was utilized for the separation of the cis- and trans enantiomers using a solvent system comprised of methanol and carbon dioxide delivered isocratically at a flow rate of 1.0 mL/min at 300 bar. Detection was achieved at 220 nm. Under these conditions, the cis-(1R,2S) indanediol and the cis-(1S,2R)-indanediol eluted after 55.21 min. and 59.59 min., respectively. The trans-(1S,2S) indanediol and the trans-(1R,2R)-indanediol eluted after 113.11 min. and 131.91 min., respectively.

Biomass measurement - Biomass determinations were performed on off-line samples by means of dry cell weights using 0.22 $\mu$m filters (Millipore Corporation, Bedford, Mass., USA).

Glucose measurement —Glucose concentrations in the supernatant were analyzed with a glucose analyzer (Mode 2, Beckman Instruments).

Purification of the cis-(1S,2R)-indanediol was achieved utilizing the following procedure: After a test run (500 mL aliquot), the remaining fermentation broth (15.5 L) was saturated with 5.58 kg NaCl and then stirred vigorously with 15.5 L ethyl acetate. Solka Floc filtering aid was added to the mixture, which was filtered through a sintered funnel. The aqueous layer of the filtrate was extracted once with ethyl acetate, and the organic layers were combined and dried over anhydrous $MgSO_4$. After filtering, the ethyl acetate was removed by rotary evaporation, and the residue was purified by silica gel chromatography (30–50% ethyl acetate-hexane) to afford 8.39 g of pure indanediol. Once combined with the front run purification, the total yield of cis-(1S,2R)-indanediol was 52%. 0.92 g of the more polar trans-(1S,2S) indanediol diastereomer was also recovered from the silica gel column.

NMR analysis of the purified products confirmed the authenticity of the cis- and trans- indanediols.

Example 5

NMR

NMR analysis of cis-(1S,2R)-indanediol was: $^1$H-NMR (DMSO-d6) δ 7.3 (m, 1H), 7.2 (m, 3H), 5.02 (d, J=6.7 Hz, 1H), 4.79 (t, 1H), 4.60 (d, J=4.6 Hz, 1H), 4.27 (quint, 1H), 2.93 (dd, J=5.5, 15.8 Hz, 1H), 2.77 (dd, J=3.7, 15.8 Hz, 1H). $^{13}$C-NMR (DMSO-d6) δ 144.0, 140.6, 127.6, 126.3,124.8, 124.7, 75.0, 72.9, 38.3.

NMR analysis of the trans-(1S,2S)-indanediol was: $^1$H-NMR (DMSO-d6) δ 7.3 (m, 1H), 7.2 (m, 3H), 5.41 (d, J=6.2 Hz, 1H), 5.19 (d, J=4.9 Hz, 1H), 4.72 (t, 1H), 4.10 (quint, 1H), 3.08 (dd, J=7.0, 15.5 Hz, 1H), 2.61 (dd, J=7.0, 15.5 Hz, 1H). $^{13}$C-NMR (DMSO-d6) δ 144.1, 139.4,127.5, 126.4, 124.5, 124.2,80.6,80.0, 38.0.

Example 6

Preparation and Isolation of cis-1S-Amino-(2R)-Indanol
A. Conversion of cis-(1S,2R)-Indandiol to cis-(1S)-Amino-(2R)-Indanol Experimental

| Materials | Amount | MW | Moles |
| --- | --- | --- | --- |
| cis-(1S,2R)-indandiol | 100 g | 150.18 | 0.66 |
| 20% oleum (sulfuric acid/sulfur trioxide | 66.2 mL | 98.08 | 1.33 |
| Acetonitrile | 633.3 mL | | |
| Water | 1000 mL | | | cis-(1S,2R)-Indandiol (100 g, 0.66 mole) was added to acetonitrile (633 mL) at 25° C. then cooled to −25 to −30° C. A solution of 20% oleum (66.2 mL, 1.33 mole) was added, while maintaining the temperature below −10° C. After the addition was completed, the mixture was warmed to 200° C., aged for 1.5 h, then water was added (1000 mL). The acetonitrile solvent was distilled until the internal temperature reached approximately 100° C. The mixture was aged at this temperature for 4.5 h. The solution was concentrated to 100 g of amino-indanol/L. Yield of 86.7%, at >99% ee.

B. Isolation of (-) cis-Aminoindanol Using Reverse Ion Pairing Extractive Workup of the Ritter Solution Starting From Diol

| Materials | Amount | MW | Moles |
| --- | --- | --- | --- |
| Step A Product | 548.7 g (50.0 g cis-aminoindanol | 149.2 | 0.335 |
| 1-butanol | 501 mL | | |
| 50% NaOH | 145 mL | 40 | |
| Water | 625 mL | | |
| L-tartaric acid | 60.0 g | 150.1 | 0.4 |

Into a 2 liter round-bottom flask equipped with a thermometer and over-head stirrer was placed 548.7 g of solution from the Ritter (50.0 g cis-aminoindanol from Step A) and 167 mL of 1-butanol. The addition of 50% NaOH was started while maintaining temperature below 40° C. with a water bath. This addition was continued until the pH was greater than 12. A total of 103 mL of 50% NaOH was added. The mixture darkened during the addition.

The mixture was placed in a separatory funnel, and the layers separated. The aqueous layer was then extracted with 2 ×167 mL 1-butanol. The three organic layers were combined and extracted with a solution of 60.0 g L-tartaric acid (1.2 mole equivalents) in 250 mL of water. The layers were separated and the organic layer was further extracted with 3 ×125 mL of water. The combined aqueous layer was then concentrated under vacuum to 220 mL. Some solids had begun to precipitate.

The concentrate was rinsed into a 500 mL round-bottom flask equipped with a thermometer and over-head stirrer with 30 mL of water. The addition of 50% NaOH was started. During the addition, the temperature was maintained below 45° C. with a water batch. The cis-aminoindanol started to crystallize between pH 8 and 9. The addition was continued until the pH was greater than 12. A total of 42 mL of 50% NaOH was added. The mixture was slowly cooled to 0–5° C., and aged for 2 hours, filtered (the filtration was slow) and washed with 150 mL of 0–5° C. water. Dry in a vacuum oven with a nitrogen purge at 45° C. for 18 hours. Yield of (-)cis-anminoindanol: 45.74 g (96.6 wt %); 2.1% trans-aminoindanol.

C. Isolation of (-)-cis-Aminoindanol Using A Dowex 50 ×8 Resin
Column Workup of the Ritter Solution Starting From Diol Experimental

| Materials | Amount | MW | Moles |
| --- | --- | --- | --- |
| Step A Product | 550 mL (50.0 g cis-aminoindanol) | 149.2 | 0.335 |
| Dowex 50 × 8 (100 mesh) resin | 500 mL (in water) | | |
| 50% NaOH | 34.5 g | 40 | |
| Water | 600 | | |
| 20% MeCN in water | 2175 | | |

A 500 mL Dowex 50 ×8 (100 mesh) resin column was set up. The column was washed, then back washed with water. The diol Ritter solution (50.0 g cis-aminoindanol in 550 mL Product of Step A) was loaded onto the column with a flow rate of 1.5 bed volumes per hour. The column was then washed with 600 mL of water. There was less than 1% breakthrough.

At first, the elution was tried using NaCl but this was not efficient. A total of 12.3 g of cis-aminoindanol was recovered. The column was washed with 500 mL of 20% MeCN in water followed by the elution with NaOH below.

Dissolve 20.3 g of 50% NaOH in 250 mL of 20% MeCN in water. Pump the solution up flow onto the column. Follow with a 100 mL 20% MeCN line rinse. Let stand for 1.75 hours. Start eluting the column with a 1.5–2 bed volume flow rate. When the solvent reaches the resin bed, elute with 750 mL of 20% MeCN in water. The total cis-aminoindanol eluted was 16.7 g.

Dissolve 11.5 g of 50% NaOH in 250 mL of 20% MeCN in water. Pump the solution up flow onto the column. Follow with a 100 mL 20% MeCN line rinse. Let stand for 1.75 hours. Start eluting the column with a 1.5–2 bed volume flow rate. When the solvent reaches the resin bed, elute with 750 mL of 20% MeCN in water. The total cis-aminoindanol eluted with 16.7 g.

Dissolve 2.7 g of 50% NaOH in 250 mL of 20% MeCN in water. Pump the solution onto the column. Start eluting the column with a 1.5–2 bed volume flow rate. When the solvent reaches the resin bed, elute with 500 mL of 20% MeCN in water. The total cis-aminoindanol eluted was 3.0 g.

The pH of the combined eluents from the first two elutions was adjusted to 2.95 with concentrated HCl. The solution was then concentrated to 228 mL under vacuum. This solution was then used in various crystallization experiments.

The total recovery of cis-aminoindanol from the NaCl and NaOH elutions was 48.7 g.

What is claimed is:

1. A process for preparing cis-(1S,2R)-indanediol comprising:
   (A) fermenting a culture medium containing a yeast strain selected from the group consisting of *Trichosporon cutaneum* MY 1506 (ATCC 74440) and mutants thereof and 1,2-indanedione to form cis-(1S,2R)-indanediol; and
   (B) recovering cis-(1S,2R)-indanediol from the culture medium.

2. The process of claim 1, wherein the cis-(1S,2R)-indanediol is formed with an enantiomeric excess of at least about 99%.

3. The process of claim 1, wherein recovering comprises separating the cis-(1S,2R)-indanediol from trans-indanediol diastereomer by-product.

4. The process of claim 3, wherein recovering further comprises separating the cis-(1S,2R)-indanediol from its cis-(1R,2S)-indanediol enantiomer, the cis-(1S,2R)-indanediol being essentially free of any stereoisomer.

5. The process of claim 2, wherein recovering comprises separating the cis-(1S,2R)-indanediol from trans-indanediol diastereomer by-product.

6. The process of claim 5, wherein recovering further comprises separating the cis-(1S,2R)-indanediol from its cis-(1R,2S)-indanediol enantiomer, the cis-(1S,2R)-indanediol being essentially free of any stereoisomer.

7. The process of claim 1, wherein the yeast strain is *Trichosporon cutaneum* MY 1506 (ATCC 74440).

8. The process of claim 7, wherein the cis-(1S,2R)-indanediol is formed with an enantiomeric excess of at least about 99%.

9. A process for preparing (1S)-amino-(2R)-indanol comprising
   (A) fermenting a culture medium containing a yeast strain selected from the group consisting of *Trichosporon cutaneum* MY 1506 (ATCC 74440) and mutants thereof and 1,2-indanedione to form cis-(1S,2R)-indanediol;
   (B) recovering cis-(1S,2R)-indanediol from the culture medium;
   (C) mixing about one equivalent of the recovered cis-(1S-2R)-indanediol with excess acetonitrile and maintaining the mixture at a temperature of from about −40° C. to about 25° C.; and
   (D) adding to the mixture excess equivalents of strong acid and maintaining the mixture at a temperature of from about −40° C. to about 25° C. to form (1S)-amino-(2R)-indanol.

10. The process of claim 9, wherein the yeast strain is *Trichosporon cutaneum* MY 1506 (ATCC 74440).

\* \* \* \* \*